United States Patent [19]

Bowersock et al.

[11] Patent Number: 5,352,448
[45] Date of Patent: Oct. 4, 1994

[54] ORAL ADMINISTRATION OF ANTIGENS

[75] Inventors: Terry L. Bowersock, Lafayette, Ind.; Waleed S. W. Shalaby, Mt. Pleasant, S.C.; William E. Blevins, Offerbem, Ind.; Michel Levy, West Lafayette, Ind.; Kinam Park, West Lafayette, Ind.

[73] Assignee: Purdue Research Foundatioin, West Lafayette, Ind.

[21] Appl. No.: 916,533

[22] Filed: Jul. 20, 1992

[51] Int. Cl.⁵ ............... A61K 39/00; A61K 47/34; A61K 9/16; A61K 9/22
[52] U.S. Cl. .................... 424/438; 424/426; 424/486; 424/487; 424/435; 424/434; 424/255.1; 424/234.1; 424/280.1; 424/823
[58] Field of Search .............. 427/88, 92, 424, 426, 427/486, 487, 435, 436, 438

[56] References Cited

U.S. PATENT DOCUMENTS

| | | | |
|---|---|---|---|
| 3,551,556 | 12/1970 | Kliment et al. | 424/487 |
| 3,880,990 | 4/1975 | Bauer | 424/438 |
| 4,001,389 | 1/1977 | Fildes | 424/438 |
| 4,178,361 | 12/1979 | Cohen et al. | 424/487 |
| 4,220,152 | 9/1980 | Dresbeack | 424/439 |
| 4,693,887 | 9/1987 | Shah | 424/486 |
| 4,749,576 | 6/1988 | Lee | 424/486 |
| 4,777,033 | 10/1988 | Ikura et al. | 424/487 |
| 4,780,315 | 10/1988 | Wu et al. | 424/438 |
| 4,801,457 | 1/1989 | Heller et al. | 424/462 |
| 5,147,646 | 9/1992 | Graham | 424/424 |

OTHER PUBLICATIONS

Heller et al. "Controlled Release of Water Soluble Macromolecules from Bioerodible Hydrogels" Biomaterials 4(4) 1983, pp. 262-266.

Primary Examiner—Christine M. Nucker
Assistant Examiner—Chris Dubrule
Attorney, Agent, or Firm—Barnes & Thornburg

[57] ABSTRACT

An oral vaccine formulation is provided for stimulation of an immune response in gut-associated lymphoid tissues. The formulation comprises an enzymatically degradable antigen in a hydrogel matrix. In ruminant species, the vaccine formulation, upon oral administration, is formed to pass through the rumen without substantial hydration and then into the post-ruminal portion of the digestive tract where the antigen is released for contact with the gut-associated lymphoid tissue.

10 Claims, No Drawings

ORAL ADMINISTRATION OF ANTIGENS

BACKGROUND AND SUMMARY OF THE INVENTION

This invention relates to a method for stimulating a mucosal immune response. More particularly, this invention relates to the use of hydrogels (water swellable, cross-linked polymers) as vehicles for delivering antigens to the mucosa-associated lymphoid tissue of the gut.

Mucosal surfaces are the sites of entry of most infectious agents and hosts. Therefore, mucosal immunity is important as the first line of defense against infectious agents. It prevents attachment of pathogens to the mucosal epithelium, neutralizes viruses and bacteria toxins, and allows other aspects of the immune system to phagocytose and remove pathogens from the mucosal site. The mucosa-associated immune system functions to prevent the penetration of microbes into the internal regions of the body.

Direct application of antigens to a mucosal surface is the best way to induce a local immune response. However, this is not always possible or practical either because of the handling involved or because the toxicity of the antigens to the mucosal surface. Local immunity can also be induced by the stimulation of the common mucosal immune system (MALT), a network whereby all mucosal sites are linked to each other immunologically. When the mucosa-associated lymphoid tissue of the gut or lung is exposed to an antigen, lymphocytes migrate to all other mucosal sites and produce antibodies. A population of memory lymphocytes is also induced which provides antibodies at a later time in response to the antigen.

The greatest accumulation of lymphoid tissue in MALT and in the body is the gut-associated lymphoid tissue (GALT) located in the intestines. These lymphoid tissues contain functional T and B lymphocytes and antigen-presenting accessory cells. In contrast to the systemic lymphoid tissues of the body, the B lymphocyte population of GALT includes a significant population of cells which are committed to the synthesis of IgA class antibodies. This antibody type is not effectively induced through conventional intramuscular or subcutaneous immunization. The lymphoid tissue is separated from the lumen of the gut by a layer of epithelial cells which are interspersed with antigen-presenting accessory cells. These specialized cells actively internalize samples from the lumenal space, and pass the samples to the underlying lymphoid cells. Exposure of GALT to antigen compounds triggers the clonal expansion of specific B and T lymphocytes. The IgA committed B lymphoblasts migrate through the roesenteric lymph nodes resulting in enhanced immune responses in all mucosal sites including the intestine, lung, mouth, eye, mammary gland, and the genitourinary tract. Thus, stimulation of GALT by oral vaccines can result in the prevention of infectious diseases at a variety of mucosal surfaces.

Timely vaccination of livestock can be a critical aspect of effective farm management. Respiratory disease of viral and secondary bacterial etiology can spread rapidly through animal herds. Although stimulation of mucosal immunity can be achieved by intranasal administration or local injection into mucosal sites, such vaccination techniques typically require individual handling and restraint of each animal. Oral vaccination is a particularly cost effective way for livestock producers to vaccinate or treat a large number of animals at one time with minimal stress or labor. This is especially true when oral administration of the vaccine can be effected through ingestion by the animals during the course of feeding. Further, oral vaccines can be manufactured more cost effectively than parenterally administered vaccine formulations because of the fewer purification steps needed to generate an oral vaccine. Oral vaccination also offers the advantage of fewer side effects such as fever or other injection reactions.

In spite of the advantages deriving from use of oral vaccines, the use and efficacy of orally administered vaccines has been hampered by degradation of the vaccine as it passes through the digestive tract. Most antigenic compounds possess peptide bonds in their configuration that are readily decomposed and denatured by the gastric acidity and proteolytic enzymes of the gut. Drug delivery systems have been proposed to protect orally ingested antigenic compounds from enzymatic or hydrolytic degradation. These delivery systems involve coating the vaccine in gelatin capsules or other coatings that are not removed until passage into the intestine. Prior art also describes the use of biodegradable microspheres for delivering vaccines to the gut-associated lymphold tissues. These microspheres, being a maximum size of 10 micrometers in diameter, are directly taken up into the lymphold tissues to stimulate an immune response.

Bovine Respiratory Disease Complex costs the cattle industry in the United States over one hundred million dollars a year. Conventional vaccination strategies have not been successful in preventing the disease. Cattle are usually vaccinated at sale barns or at stock yards when they have already been stressed and exposed to a number of pathogens. A better time to vaccinate cattle is before they are sold, optimally when they are still in the pasture. This is typically not done due to the labor required to inject each animal individually. An efficient way to vaccinate the cattle in a pasture would be through feed or water. Recent studies have shown that it is possible to stimulate antibodies to *P. haemolytica*, the most common cause of bacterial pneumonia in cattle, by stimulating GALT in cattle with bacterial antigens.

However, bovine and other ruminant species present a greater challenge to oral vaccination because the administered antigen dose has four stomachs to traverse in route to the small intestine where GALT tissues are located. To be practical, orally dosed therapeutic agents for ruminant species must meet a number of design specifications. First, the dosage form must be easy to administer, easily swallowed and not be readily regurgitated by the animal. Secondly, in terms of release rate performance, the device must deliver a therapeutically effective dose accurately and reliably without a catastrophic failure or "dose dumping." Finally, the drug and delivery device must be cost effective.

Oral vaccines have not typically been used in cattle because the harsh environment of the rumen results in microbial digestion of any unprotected antigens. The rumen is the first of four stomachs present in ruminants. It functions by fermentation digestion by bacteria action to break down cellulose and other complex nutrients. Therefore, an oral vaccine for cattle must be protected while passing through the rumen in order to deliver an effective dose of antigen to GALT in the lower gastrointestinal tract.

In accordance with this invention, hydrogels have been found to be an effective delivery vehicle or matrix capable of protecting an antigenically active vaccine formulation while it passes through the rumen. A hydrogel is a water swellable, cross-linked polymer well known to those of ordinary skill in the art. See, for example, Dresback, U.S. Pat. No. 4,220,152, issued Sep. 2, 1980, the disclosure of which is expressly incorporated herein by reference. The hydrogel dosage forms have been found to pass without substantial hydration through the rumen to become localized in the reticulum, where they are hydrated and concomitantly release the vaccine (antigenic composition) held in the hydrogel. The released vaccine is carried into the small intestine, without loss of antigenicity, where it makes contact with GALT to induce an immune response.

Additional objects, features, and advantages of the invention will become apparent to those skilled in the art upon consideration of the following detailed description of preferred embodiments exemplifying the best mode of carrying out the invention as presently perceived.

DETAILED DESCRIPTION OF THE INVENTION

In accordance with one preferred embodiment of the present invention, ruminants, such as cattle and sheep, are vaccinated through the oral administration of vaccines in hydrogel carriers.

Hydrogels are water swellable, cross-linked polymers that can be impregnated or loaded with vaccines and vaccine adjuvants such as liposomes, polymer microsphere carriers and the like. The vaccine loaded into the hydrogel is released in a controlled manner as the hydrogel becomes hydrated within an animal's digestive system. In a preferred embodiment, the present hydrogel matrix is in a pelletized form comprised of polymethacrylic acid. The hydrogel pellets are preferably synthesized by polymerizing methacrylic acid, in the presence of methylene bis-acrylamide (a cross-linking agent) and ammonium persulfate and sodium bisulfite (reaction initiators). The polymerization solution typically contains about 30 to about 50%, most preferably about 36% weight per volume monomer (methacrylic acid) and an amount of cross-linking agent ranging from about 0.01% to about 5% weight/volume. Polymerization is typically carried out in a 3–5 mm in diameter plastic cylinder. The solidified hydrogel is removed from the cylinder and cut into 2–3 mm lengths, washed in double distilled water, and dried to a hard, glassy polymer. The gels are then rehydrated in a solution containing effective amounts of the vaccine-antigen species and then dried again to a hard, glassy vaccine-impregnated gel for therapeutically effective oral delivery of the contained vaccine.

Another method of forming a vaccine-impregnated gel for oral delivery of a vaccine comprises the steps of adding an aqueous solution of the antigenic compound to a solution of monomer and cross-linker and initiating polymerization of the mixture. The monomer-antigen hydrogel solution typically consists of about 30 to about 50% weight/volume of a hydrogel forming monomer and about 0.01 to about 5% of a cross-linking agent. Alternatively, the solution comprises a cross-linker and a linear cross-linkable hydrogel-forming polymer. The antigen-containing solution is cross-linked by adding cross-linking agents or by other cross-linking initiating conditions such as exposure to gamma or UV radiation, to provide the hydrogel-antigen composition.

The volume of the individual hydrogel-vaccine pellets of this invention is not critical but it typically ranges from about 3 $mm^3$ to about 75 $mm^3$, more preferably from about 4 $mm^3$ to about 25 $mm^3$. Their air-dried density ranges from about 1.1 g/cc to about 1.4 g/cc. They typically are loaded to contain sufficient vaccine-antigen so that effective vaccination can be accomplished by oral administration of about 50 to about 500 of the hydrogel-vaccine pellets daily over time.

The hydrogel-vaccine compositions of this invention comprise an antigenic composition in an amount effective to induce an immune response by the gut-associated lymphold tissue of the small intestine. The enzymatically degradable antigenic composition is contained in a water swellable hydrogel matrix that is formed to facilitate passage through the harsh proteolytic environment of the upper digestive tract without substantial hydration.

Experimental data have shown that hydrogels prepared in accordance with this invention, but loaded with a radiopaque test material, release the entrained "load" into the abomasum, or fourth stomach, within three (3) hours after administration (see Example 1).

The hydrogel-vaccine compositions of this invention are particularly advantageous for use in ruminants. Not only do the hydrogel-vaccine compositions move quickly through the rumen, but they also are retained in the reticulum where they are hydrated. Hydration results in the slow release of the contained antigens, thereby reducing the dosage of vaccine needed to stimulate the desired immune response in the lymphold tissue. Slow release of the antigen from the hydrogel matrix extends the period of effective GALT stimulation, thereby minimizing the undesirable side effects often associated with parenterally administered vaccines at injection sites.

Transit Time and Kinetics of Release of Materials from Hydrogels

EXAMPLE 1

Hydrogel Preparation—Polymethacrylic acid (PMA) hydrogels were produced by cross-linking methacrylic acid (Aldrich Chemical Co.) with N,N'-methylenebisacrylamide (Bio-Rad Laboratories). Ammonium persulfate (Polysciences, Inc.) and sodium bisulfite (J. T. Baker Chemical Co.) were used as the initiators. The solutions were degassed and purged with nitrogen. Monomer solutions were placed into 1 ml syringe barrels. Polymerization was carried out at 60° C. for eighteen (18) hours under nitrogen. The gels were removed and cut into 5 mm in diameter $\times$ 3 mm long discs, washed in distilled deionized water and dried at 37° C. for one (1) week.

Rumen Bypass Studies—The passage of hydrogels through the rumen was studied by administering hydrogels loaded with a radiopaque material to a sheep. A sheep was used because it is a ruminant that is easier to radiograph. PMA hydrogels were loaded with the radiopaque marker, Gastrografin (diatrizoate meglumine/sodium diatrizoate, Squibb Diagnostics), and the sheep was radiographed over time to document the disposition of hydrogels as previously described. Gastrografin-loaded hydrogels were placed into two (2) 15 ml gelatin capsules and administered to a sheep using a bailing gun. Movement of the hydrogels through the upper gastrointestinal tract (GIT) and release of the Gastrografin from the gels was monitored over time by radiography.

Antigen Release Studies—The use of hydrogels as a vaccine delivery system was studied using chromium-ethylenediamine tetraacetic acid (Cr-EDTA) as a model antigen. Chromium-EDTA was chosen for this study since only 2–3% is absorbed by the ruminant gastrointestinal tract and therefore could be readily detected in the intestinal fluid. Dried PMA hydrogels were loaded with 4.3 grams of Cr-EDTA by swelling them in a 10% (weight/volume) Cr-EDTA solution for 48 hours at 37° C. Each hydrogel was loaded with about 14 mg of chromium. After loading the hydrogels were dried at 37° C. for one (1) week. The hydrogels (300 total) were placed in two (2) 15 ml gelatin capsules and administered to a sheep by bailing gun. Samples of ileal contents were collected over ninety-six (96) hours through a re-entrant cannula placed in the ileum 6 cm proximal to the ileal-cecal junction. The cannula was placed by transecting the ileum, suturing the cut ends and inserting each arm of the cannula in the proximal and distal ends. The ends of each arm of the cannula were passed through the flank by blunt dissection, clamped securely to the skin, and the two ends connected so that all intestinal contents passed through the cannula. All intestinal contents were collected for one hundred (100) hours for one study to look for hydrogels. Ileal contents were collected, poured through a 60 mesh sieve, examined for hydrogels, and the liquid portion injected into the caudal aspect of the cannula. All feces were collected for one (1) week, broken apart and passed over a 60 mesh sieve to look for the presence of hydrogels.

Atomic absorption spectrophotometry—The intestinal samples were assayed for chromium content by atomic absorption spectrophotometry. Samples of ileal contents were centrifuged at 500×g for thirty (30) minutes to separate the fibrous matter from the liquid fraction. A 0.8 ml aliquot of the supernatant was then added to 15 ml of 1N HNO$_3$ and heated for six (6) hours at 60° C. to precipitate any soluble proteins. The samples were then filtered through a 0.2 um pore size filter (Sigma). Chromium levels were detected by atomic absorption spectrophotometry (Perkin-Elmer, model-2380) at a wavelength of 357.9 nm and a slit setting of 0.7 nm. Samples containing 5 ug/ml and 15 ug/ml of chromium in 1N HNO$_3$ were used as standards.

Rumen Bypass Studies—A significant number of gels entered the reticulum by fifteen (15) minutes after administration. Approximately 60% of the gels were in the reticulum within one (1) hour. As the gels began to swell, Gastrografin was released due to its pH-dependent solubility and the outline of the organs of the upper GIT could be seen. Gastrografin was seen in the omasum and abomasum within three (3) hours. By three and one-half (3.5) hours it was difficult to see the gels as a result of the release of Gastrografin. Hydrogels appeared to remain in the reticulum; no hydrogels were seen in either the omasum or abomasum during the study.

Antigen Release Studies—The Cr-EDTA was detected in the ileum from three through ninety-six (3–96) hours after administration with peak levels at twelve through fifteen (12–15) hours. No gels were found in the ileal contents or the feces during the study.

CONCLUSIONS

This study demonstrates that hydrogels can bypass the rumen and move rapidly into the reticulum. Rumen bypass is dependent on the size and density of particles. Hydrogels too large, too small, or not dense enough would more likely become suspended in the rumen and not enter the reticulum. This was found to be the case in our preliminary studies (data not shown). The hydrogels 5 mm in diameter by 3 mm in length entered the reticulum or second stomach within fifteen (15) minutes after administration because they appeared to have the optimal size and density to bypass the rumen most efficiently. The size and density (1.40 g/cc) of the gels used in this study have been associated with short rumen retention time. Although it appears that gel retention and subsequent gel erosion may have occurred in the reticulum as a result of size discrimination at the reticulo-omasal orifice, further studies are needed to confirm this. This study showed that while retained in the upper gastrointestinal tract, hydrogels released a model antigen (Cr-EDTA) that was detectable for ninety-six (96) hours in the ileum. Detection of Cr-EDTA in the intestinal contents was probably due to its release in the upper gastrointestinal tract and not due to the hydrogels traversing the lower intestinal tract as indicated by the inability to find hydrogels in intestinal contents or feces. This study supports the hypothesis that hydrogels are suitable to deliver vaccines orally to ruminants.

EXAMPLE 2

Loading hydrogels with culture supernatants—*Pasteurella haemolytica* is the most common cause of bacterial pneumonia in cattle. The best parenteral vaccine for this organism on the market today is composed of culture supernatants. Culture supernatants (CS) contain many antigens, including a proteinaceous exotoxin (leukotoxin) 102 kd in size. Therefore, it was necessary to determine whether CS could be loaded and released from hydrogels. Hydrogels were produced as previously described. Gels were loaded with CS which had been harvested from *P. haemolytica* cultured to the active phase of growth, lyophilized, and resuspended to a 22% (weight/volume) solution. Three hundred (300) hydrogel pellets having a dried volume of about 4 to about 20 mm$^3$ were added to 100 mls of this solution and were fully hydrated over a period of about forty-eight (48) hours. Loaded gels were dried to a hard glassy consistency by placing them in a 37° C. incubator for forty-eight (48) hours.

Antigen release studies in vitro—To test for release of the CS antigens, three (3) loaded gels were placed in saline and allowed to hydrate. Eluent was removed from the gels daily for three (3) days and fresh saline placed on the gels. The eluents were tested for the presence of leukotoxin, the primary protein antigen present in CS, by SDS-Polyacrylamide Gel Electrophoresis (SDS-PAGE) analysis and Enzyme Linked Immunosorbent Assay (ELISA).

It was shown that culture supernatants of *P. haemolytica* could be absorbed into and eluted from the hydrogel; the hydrogels composition was then tested for efficacy of antigen delivery to GALT in vivo. The efficacy of this method of inoculation was tested by challenging the calves, after vaccination, with an intrabronchial inoculation of viable *P. haemolytica*.

Calf vaccine trial—Twelve (12) Holstein-Friesian four (4) month old calves were divided into two (2)

groups. Experimental calves (vaccinates) were given 300 CS-loaded hydrogels per day placed inside two (2) 15 ml gelatin boluses for five (5) days by bailing gun. Control calves (non-vaccinates) were given 300 plain hydrogels. Pulmonary lavage was performed prior to vaccination and two (2) weeks after the first oral dose of hydrogels. Serum was collected on the same days as the lavages. Antibody titers to CS pre and post vaccination were determined for serum and pulmonary lavage fluids. Three (3) weeks after the first day of vaccination each calf was challenged with an intrabronchial inoculation of 25 ml of $10^9$ CFU/ml of virulent *P. haemolytica*. Calves were monitored for clinical signs of disease. Calves which survived for seventy-two (72) hours were euthanatized and a post mortem examination performed. Lungs were scored for the percentage of pneumonic lesions, gross and histopathological lesion score, and a pneumonic index was computed by multiplying the first three (3) values together. Scores for calves were ranked by survival time and pneumonic index and the data analyzed using the Wilcoxon rank sum statistical test.

Antigen release studies—One major protein band was noted in the SDS-PAGE analysis of eluents at 102 kd, the molecular weight of the leukotoxin (data not shown). In the ELISA assay the absorbance values for the eluents indicated the presence of leukotoxin (Table 1). These results suggested that the hydrogels loaded with CS were appropriate to test in calves.

Calf challenge studies—The survival time post-challenge in hours, percent pneumonic lung, gross and histopathological lesion scores for each calf is shown in Table 2. There was a significantly lower percentage of pneumonic lung, lower gross lesion score, lower histopathological lesion score, and pneumonic index when evaluated in combination with survival time for vaccinated calves compared to non-vaccinates as shown in Table 3. Wilcoxon rank sum analysis demonstrated that vaccinated animals had significantly less lesions and greater survivability than non-vaccinated controls.

Immunoglobulin titers—There was an increase in CS specific IgM, IgG$_1$, and IgA in pulmonary lavage fluids in vaccinated calves compared to non-vaccinates (Table 4). There was no change in any CS specific serum antibody isotypes in vaccinated calves. These results suggest that a primary mucosal stimulation occurred. A greater immune response may have been detected if the calves had been administered subsequent inoculations either orally, intranasally, or parenterally. Enhanced immune responses at mucosal sites have been documented for orally primed animals.

Passage of hydrogels—Feces were examined during the time calves were being vaccinated for the presence of hydrogels. Five (5) hydrogels, mildly hydrated to non-hydrated, were found in feces. At post mortera the entire gastrointestinal tract was examined and no hydrogels were found. This suggests that most hydrogels were probably retained in the reticulum and were eroded due to the extremely coarse consistency of the ingesta. The CS were probably released over time as indicated by the chromium release studies and the hydrogels eroded slowly as well. This hypothesis cannot be proven until further tests are performed. It is possible the hydrogels were eroded from the time they entered the reticulum and that is how the CS were released. However, this is unlikely as the in vitro studies showed that CS are released over at least three (3) days time. Chromium studies also showed that the hydrogels can release a product over twenty-four hours. Overall, the desired result of release of the CS to stimulate GALT was achieved.

TABLE 1

ELISA RESULTS OF LEUKOTOXIN ELUTED FROM GELS HYDRATED IN PHOSPHATE BUFFERED SALINE FOR THREE (3) DAYS.

| Sample Tested | Absorbance Reading |
|---|---|
| Culture supernatant used to load gels | .421 |
| Tryptic soy broth | .207 |
| Eluent day 1 | .391 |
| Eluent day 2 | .351 |
| Eluent day 3 | .4682 |

TABLE 2

SURVIVAL AND POST-MORTEM RESULTS OF CALVES FOLLOWING CHALLENGE BY *P. HAEMOLYTICA*

| Trial | ID | Treatment Group | Survival (hours) | Percentage Pneumonic Lung | Gross Lesion Score | Histopath Lesion Score | Pneumonic Index |
|---|---|---|---|---|---|---|---|
| 1 | 74 | V | 3.5 | 0.4 | 6.0 | 3.5 | 8 |
| 1 | 77 | V | 3.5 | 2.1 | 6.0 | 5.8 | 71 |
| 1 | 78 | V | 23* | 25.8 | 12.5 | 16.8 | 5105 |
| 1 | 75 | C | 3.5 | 53.7 | 15.0 | 6.2 | 4994 |
| 1 | 76 | C | 3.5 | 61.4 | 13.5 | 7.7 | 6394 |
| 1 | 80 | C | 72** | 24.2 | 17.0 | 4.4 | 1810 |
| 2 | 82 | V | 72** | 44.2 | 9.5 | 1.2 | 487 |
| 2 | 84 | V | 72** | 28.8 | 8.5 | 0.9 | 211 |
| 2 | 87 | V | 72** | 31.3 | 10.5 | 1.6 | 526 |
| 2 | 81 | C | 12 | 100 | 11.0 | 3.5 | 3850 |
| 2 | 83 | C | 12 | 100 | 10.0 | 6.8 | 6830 |
| 2 | 85 | C | 20 | 100 | 10.0 | 2.5 | 2500 |

C = non-vaccinated control animals
V = vaccinated animals
* = euthanized because moribund
** = euthanized at end of trial
Gross lesion score was based on the severity of parameters (fibrin, edema, consolidation, etc.) with a maximum score of 24 for the most severe lesions. Histopathological lesion score was based on the severity of 14 different parameters (necrosis, fibrin, etc.) with a maximum score of 42 for the most severe lesions. Pneumonic index was computed by multiplying the percentage pneumonic ling × gross lesion score × histopathological lesion score.

TABLE 3

RANKING WITHIN TRIAL BY SURVIVAL AND PNEUMONIC INDEX

| Trial | Rank | ID | Survival | Pneumonic Index | Treatment Group |
|---|---|---|---|---|---|
| 1 | 1 | 76 | 3.5 | 6349 | C |

TABLE 3-continued

RANKING WITHIN TRIAL BY
SURVIVAL AND PNEUMONIC INDEX

| Trial | Rank | ID | Survival | Pneumonic Index | Treatment Group |
|---|---|---|---|---|---|
| 1 | 2 | 75 | 3.5 | 4994 | C |
| 1 | 3 | 77 | 3.5 | 71 | V |
| 1 | 4 | 74 | 3.5 | 8 | V |
| 1 | 5 | 78 | 23 | 5105 | V |
| 1 | 6 | 80 | 72 | 1810 | C |
| 2 | 1 | 83 | 12 | 6830 | C |
| 2 | 2 | 81 | 12 | 3850 | C |
| 2 | 3 | 85 | 20 | 2500 | C |
| 2 | 4 | 87 | 72 | 526 | V |
| 2 | 5 | 82 | 72 | 487 | V |
| 2 | 6 | 84 | 72 | 211 | V |

C = non-vaccinated control animals
V = vaccinated animals
Key: Rank 1 = worst; Rank 6 = best
Survival + Percent Pneumonic Lung P = .040
Survival + Gross Lesion Score P = .035
Surival + Histopathology Lesion Score P = .045
In trial 2, all C's rank above all V's. In trial 1, only one C breaks this pattern. For both trials together, the exact P-value for the rankings is P = .045; thus there is a statistically significant evidence ($P < .05$) that vaccinated animals had less severe lesions following challenge.

TABLE 4

| ANTIBODY RESPONSE IN CALVES | | | | |
|---|---|---|---|---|
| | PULMONARY | | SERUM | |
| | Vaccinate | Control | Vaccinate | Control |
| IgM | 1.60* | 1.04 | 1.491** | 1.510 |
| IgG1 | 1.83 | 1.46 | .417 | .408 |
| IgG2 | 1.01 | 1.08 | .041 | .050 |
| IgA | 1.25+ | 0.78 | .011 | .017 |

BAL = Bronchoalveolar lavage
*Ratio of specific antibody/total immunoglobulin post-vaccination to the same ratio pre-vaccination. Vaccinates were vaccinated for 5 days by oral inoculation of culture supernatants absorbed into polymeric beads. Control calves were given plain beads. Post-vaccination BAL was performed 2 weeks after first oral dose was given which was the same day pre-vaccination BAL was performed.
+P = 0.17
**Mean absorbance value of serum 2 weeks post-vaccination as determined by ELISA using culture supernatants as antigen.

CONCLUSIONS

Hydrogels were successfully loaded with CS containing a mixture of bacterial antigens including the proteinaceous exotoxin 102 kd in size. Loaded hydrogels released the antigens in the gastrointestinal tract and stimulated an immune response that resulted in protection of the lungs of calves challenged with viable P. haemolytica. It is not clear what factor(s) of the immune system were responsible for the protection. Even though there was no clearly significant increase in pulmonary isotypic antibodies, three (3) isotypes did increase in vaccinated calves compared to controls. The pulmonary IgA titer increased the most. The lack of significance is due to great variability between calves which are outbred and naturally possess a varied genetic pool. Further statistical analysis to evaluate the immune response is in progress. This is the isotype which is usually seen in mucosal surfaces following stimulation of GALT. Pulmonary IgA could reduce the severity of pneumonia by decreasing the binding of bacteria to epithelial cells in the lung thereby preventing colonization and infection, or by neutralizing the leukotoxin and preventing damage to neutrophils and macrophages in the lung. Release of oxidative radicals by damaged phagocytes can contribute to the damage to the lung parenchyma. The role of mucosal immunity in pneumonic pasteurellosis is not well understood at this time. Results of this study suggest mucosal immunity is more important than humoral antibodies which were unchanged in vaccinated calves.

Humoral immunoglobulin responses to P. haemolytica vaccines have been found to not be associated with protection. The results of this study are consistent with those of previous studies in which intraduodenal administration of CS of P. haemolytica resulted in enhanced pulmonary antibodies in calves. The immunity and decreased lesions in vaccinated calves in the present study show that antigen release by hydrogels was as effective as intraduodenal inoculation in stimulating mucosal immunity in calves.

This study showed that oral administration of hydrogels to ruminants can result in immunity at distant mucosal sites. Studies are under way to determine what other antigens can be loaded into hydrogels and retain their immunogenicity when released into the lower gastrointestinal tract. Hydrogels provide a practical, safe, economical way to deliver oral vaccines to a large number of animals to prevent diseases which begin at a mucosal surface.

Although the invention has been described in detail with reference to certain preferred embodiments, variations and modifications exist within the scope and spirit of the invention as described and defined in the following claims.

We claim:

1. An oral vaccine composition for ruminant species said composition comprising
   an antigenic composition in an amount effective to induce an immune response in gut-associated lymphoid tissue of said ruminant species in a delivery vehicle consisting essentially of a water swellable hydrogel matrix in the form of pellets having a volume of about 3 to about 75 $mm^3$ and an air-dried density of about 1.1 to about 1.4 g/cc for hydration int he post-ruminal portion of the digestive tract of said species and release of said antigenic composition for contact with the gut-associated lymphoid tissue.

2. The composition of claim 1, wherein the hydrogel matrix is combined with the antigenic composition by hydrating the hydrogel matrix in a solution of the antigenic composition and drying the hydrated matrix.

3. The composition of claim 1, wherein the antigenic composition is a mixture of antigens obtained from the culture supernatant of a bacterial culture.

4. A method of vaccinating ruminants by stimulating the gut-associated lymphoid tissue with an antigenic composition said method comprising the step of orally administering a vaccine composition in accordance with claim 1.

5. The method of claim 4, wherein the vaccine composition is administered in admixture with animal feed.

6. The method of claim 4, wherein the vaccine composition is administered in a bolus dosage form.

7. An orally administered ruminant vaccine composition comprising a proteolytically degradably antigenic composition in a delivery vehicle consisting essentially of a swellable hydrogel matrix in the form of pellets having a volume of about 3 to about 75 $mm^3$ and an air-dried density of about 1.1 to about 1.4 g/cc, said antigenic composition releasable from said hydrogel matrix upon swelling of the matrix in the post-ruminal portion of the ruminant digestive tract.

8. A method of forming the composition of claim 1, said method comprising the steps of
   forming an aqueous solution comprising the antigenic composition, about 30 to about 50 percent weight of a hydrogel forming monomer or a cross-linkable hydrogel-forming polymer, and about 0.01 to about 5% of a cross-linking agent, initiating hydrogel formation, and drying the resulting hydrogel-antigen composition.

9. A method of forming the composition of claim 1, said method comprising the steps of forming the hydrogel matrix in a pelletized form, drying the hydrogel pellets, forming an aqueous solution of the antigenic composition, combining the hydrogel pellets with the aqueous solution and allowing the pellets to rehydrate, removing the pellets from the aqueous solution and drying the pellets.

10. A method of vaccinating ruminant species by stimulating the gut-associated lymphoid tissue with an antigenic composition, said method comprising the step of orally administering to said ruminant species a vaccine composition comprising the antigenic composition in a delivery vehicle consisting essentially of a hydrogel matrix in the form of pellets having a volume of about 3 to about 75 mm$^3$ and an air-dried density of about 1.1 to about 1.4 g/cc, swellable in the post-ruminal portion of the digestive tract of the ruminant species with resultant release of the antigenic composition for stimulation of the gut-associated lymphoid tissue of said ruminant species.

* * * * *